United States Patent [19]

Bailey et al.

[11] Patent Number: 5,211,558

[45] Date of Patent: May 18, 1993

[54] PORTABLE DENTAL WORKSTATION

[75] Inventors: James R. Bailey, Indianapolis; C. Robert Schrock, Greenwood, both of Ind.

[73] Assignee: International Equipment & Supply Corp., Indianapolis, Ind.

[21] Appl. No.: 800,256

[22] Filed: Nov. 29, 1991

[51] Int. Cl.$^5$ .............................................. A61G 15/00
[52] U.S. Cl. .......................................... 433/77; 433/98
[58] Field of Search .................... 433/77, 79, 92, 98, 433/99, 101

[56] References Cited

U.S. PATENT DOCUMENTS

| | | | |
|---|---|---|---|
| 3,081,542 | 3/1963 | Sherfey | 433/77 |
| 3,476,144 | 11/1969 | Krantz | 433/92 |
| 3,553,840 | 1/1971 | Bordelon | 433/77 |
| 3,636,633 | 1/1972 | Fuller et al. | 433/77 |
| 3,734,122 | 5/1973 | Cousins | 433/98 |
| 4,160,323 | 7/1979 | Tracy | 433/77 |
| 4,173,827 | 11/1979 | Austin, Jr. | 433/98 |
| 4,217,009 | 8/1980 | Suter | 433/79 |
| 5,013,240 | 5/1991 | Bailey et al. | 433/77 |

FOREIGN PATENT DOCUMENTS

| | | |
|---|---|---|
| 0094470 | 5/1982 | European Pat. Off. |
| 1251915 | 11/1971 | United Kingdom |
| 2165760 | 4/1986 | United Kingdom |

*Primary Examiner*—John J. Wilson
*Attorney, Agent, or Firm*—Woodard, Emhardt, Naughton, Moriarty & McNett

[57] ABSTRACT

A portable dental apparatus. A main housing includes a plurality of wheels mounted therebeneath. A control panel on the main housing includes a variety of controls for operating a plurality of dental tools removably and suspendedly mounted to a holder in turn movably mounted to the main housing. A storage cavity formed in the housing allows storage of the holder and tools when the portable dental apparatus is in a transport state. The tools are connected by a plurality of lines to a plurality of drive and power components located in the interior of the main housing. A lid hingedly mounted atop the control panel may be opened revealing the controls for the tools. An X-ray display screen and amalgamator are provided respectively on the lid and control panel.

A modular vacuum unit with a built in cooling fan and thermo protector is also provided. Additionally, the portable dentist apparatus includes an improved pressurized air and water distribution manifold and an improved waste water storage receptacle. Furthermore, the waste water receptacle has means provided to automatically shut off the vacuum motor when the receptacle is full or when the receptacle is placed improperly in the unit. The receptacle also has means provided to baffle fluids flowing into the receptacle such that fluids will not back flow into the vacuum motor.

11 Claims, 7 Drawing Sheets

PORTABLE DENTAL WORKSTATION

BACKGROUND OF THE INVENTION

This invention is in the field of dental tools.

DESCRIPTION OF THE PRIOR ART

A number of conventional dental tools including high and low speed drills, syringe and suction devices, and light curing wands are utilized in the delivery of dental services. These tools are powered by electric components including a compressor, a vacuum pump and light source. Traditional tools including X-ray view screens and amalgamators are also required in the practice of dentistry. In the standard dental office, the aforementioned tools are removably mounted to a heavy stationary post, and are further connected to various electric and fluid lines to various sources of power. As such, it is necessary for the patient to visit the permanent dental site to facilitate receiving dental services. It can be appreciated that in many cases the visit to the dental office is of great inconvenience and in certain instances impossible for the patient.

A device that serves many of these needs has been patented by the present inventor as U.S. Pat. No. 5,013,240. This patent issued to Bailey, et al. discloses a portable dental apparatus. This apparatus provides many of the features found in the present invention it lacks, however, many of the other features and improvements of the present invention. Examples of such features include modular construction of the fan motor, a pressurized air water distribution manifold, and an improved waste water storage container that provides for automatic shutoff of the vacuum motor should the receptacle become full or should it be positioned improperly within the unit.

The applicant is aware of other patents which may be pertinent to the present invention. U.S. Pat. No. 4,217,009 to Suter discloses a dental cabinet appliance. The Suter device is capable of positioning dental instruments at a location convenient to either a seated or standing dentist.

U.S. Pat. No. 4,160,323 to Tracy discloses a portable dental cabinet. The Tracy dental unit provides physical support for dental operations during a long period of time when the operations are conducted in a remote or out of office areas.

U.S. Pat. No. 3,081,542 to Sherfey discloses a mobile dental unit. The Sherfey device provides for specialized operating equipment which can be taken to the patient if the patient cannot visit a professional office.

European Patent No. 0 094 470 to Bernaz discloses a portable dental station contained within a suitcase like container. This device provides a solid air tight casing enclosing a stainless steel miniature bench for layout of instruments on top of an electronics package.

United Kingdom Pat. No. 2 165 760A discloses a portable dental unit. The dental unit is housed in a case with a base tray, a lid, a rack of dental instruments, an electric motor, water reservoir, and air reservoir.

United Kingdom Patent No. 1 251 915 to Chasen and Miller discloses a portable dental apparatus. This device is an apparatus which makes it possible to carry out dental operations under conditions where an office of a practicing dentist is not readily available.

We have designed a portable dental apparatus allowing the dentist to perform the various dental services at the residence or other close location to the patient. Such a portable dental apparatus is particularly convenient when the patient is in the hospital or rest home or when located at a temporary field installation such as found in the military.

SUMMARY OF THE INVENTION

One embodiment of the present invention is a portable dental apparatus comprising a portable main housing having an interior, a transport device beneath the main housing operable to allow the portable dental apparatus to have an in-use stationary state and a transport state, a dental tool holder means on the main housing, a plurality of dental tools removably mountable on the dental tool holder, drivers mounted within the interior operable to drive the dental tools including a pressurized air source and a pressurized water source, a connector connected between the drivers and the plurality of dental tools including a distribution manifold and valves disposed between the drivers and the plurality of dental tools wherein the distribution manifold is substantially solid and includes a plurality of bores, wherein the valves are mounted on the distribution manifold to allow pressurized air and pressurized water to pass from the distribution manifold, through the valves, and back into the manifold, and wherein pressurized air and pressurized water are distributed from the pressurized air source and the pressurized water source through the bores and the valves to the plurality of dental tools.

It is an object of the present invention to provide a portable dental apparatus.

A further object of the present invention is to provide a portable means for transporting a plurality of dental tools in a ready to use condition.

A further object of the present invention is to provide a portable dental apparatus having a distribution manifold which minimizes the need for hoses and tubing and which provides a direct mounting means for valves and controls to distribute pressurized air and water to dental tools.

A further object of the present invention is to provide a portable dental apparatus having a waste water receptacle which prevents a suction source from operating unless the receptacle is sealingly engaged to the the vacuum hose.

A further object of the present invention is to provide a portable dental apparatus having a waste water receptacle which prevents a suction source from operating when the receptacle is full.

A further object of the present invention is to provide a portable dental apparatus having a waste water receptacle which provides a tubular baffle to settle waste water as it enters receptacle.

A further object of the present invention is to provide a portable dental apparatus having a vacuum source which vents outside the apparatus to prevent fowling of the intake air.

A further object of the present invention is to provide a portable dental apparatus having modular construction to allow for easy access to the drivers and aid in limiting apparatus down time.

Related objects and advantages of the present invention will be apparent from the following description.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
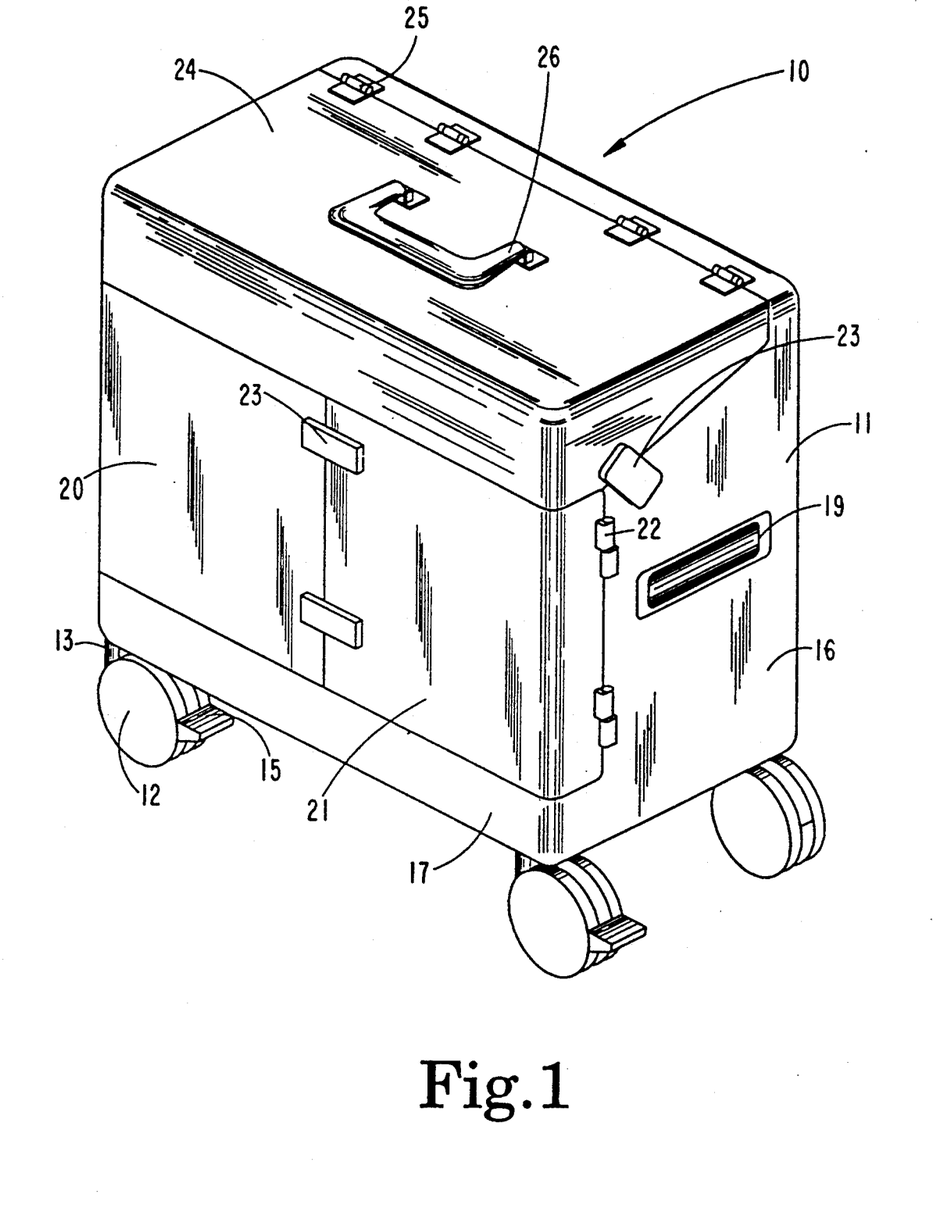
FIG. 1 is a perspective view of the preferred embodiment of the portable dental apparatus incorporating the present invention.

Referring now more particularly to FIG. 1, there is shown the preferred embodiment of the portable dental workstation incorporating the present invention. Workstation 10 has a main housing 11 mounted atop four conventional wheels 12 each being rotatable to allow the apparatus to be moved across a horizontal surface. Each wheel is pivotably mounted about a vertical shaft 13 allowing each wheel to pivot facilitating ease of movement. Further, each front wheel includes a brake handle 15 which may be moved downwardly thereby locking the wheel and preventing rotation of the wheel.

Figure 4:
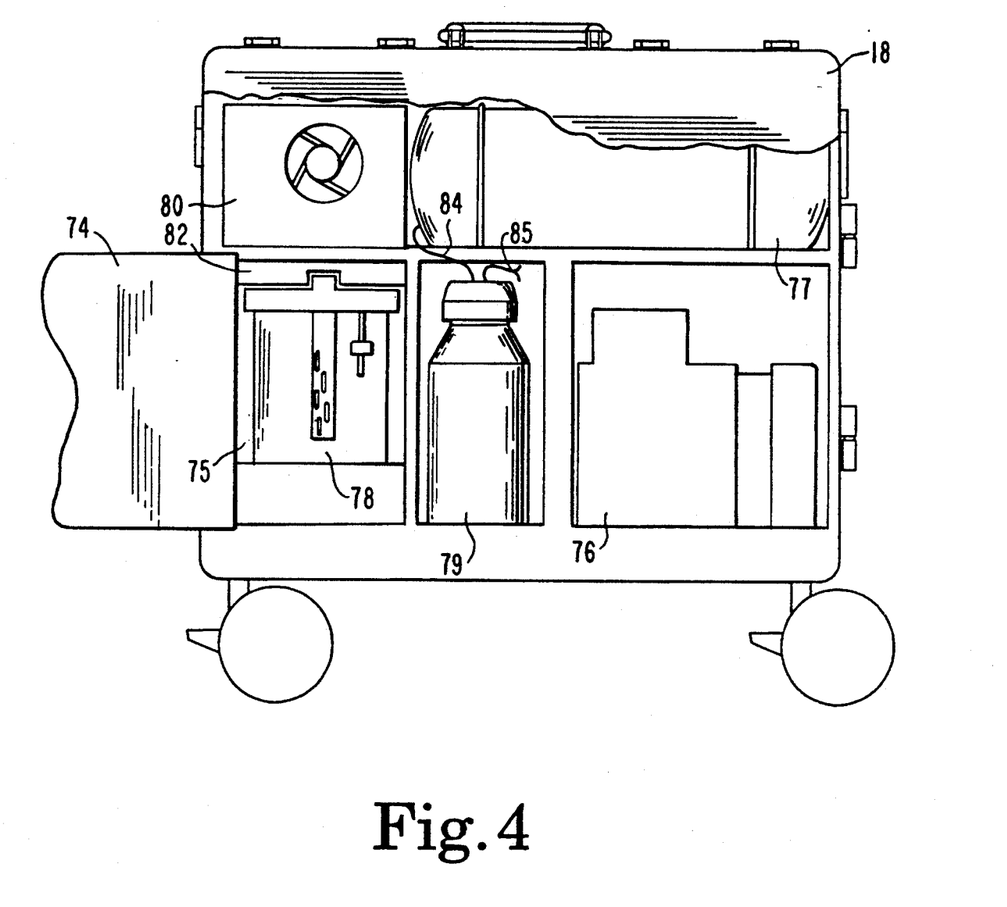
FIG. 4 is a fragmentary back view of the apparatus of FIG. 1 with the rear access door open displaying the various drive components.

Main housing 11 includes a pair of end walls 16 integrally joined to a lower front wall 17 and a rear wall 18 (FIG. 4). Likewise, the end walls, lower front wall and rear wall are integrally joined to a bottom wall 14 (FIG. 2) having wheels 12 rotatably mounted thereto. A recessed handle 19 is formed in each end wall 16.

All components of main housing 11 are connected with fasteners to the apparatus chassis. The amount of fasteners is limited however so as to provide easy access to the internal workings of the portable dental apparatus. This easy access enables service and maintenance of the apparatus with a minimum of down time.

A pair of front doors 20 and 21 have opposite ends pivotably mounted by conventional hinges 22 to the end walls of the main housing. Hinges 22 are conventional lift off hinges so that the door may be easily removed. Doors 20 and 21 are shown in FIG. 1 in a closed position with the mutually facing vertically extending edges of the doors in contact and secured together by a pair of clasps 23. Clasps 23 are conventional in design and are mounted to door 21 being operable to releasably engage a mating component mounted to door 20. By releasing clasps 23 the doors may be pivoted about hinges 22 to the open position revealing the various tools mounted within the main housing. A lid 24 is pivotably mounted by a plurality of conventional hinges 25 in turn secured to main housing 11. A handle 26 is provided on the upper surface of lid 24 to facilitate lifting of the portable dental workstation. Likewise, an additional pair of clasps 23 are mounted to the opposite end walls 16 of the main housing and are operable to releasably engage complimentary components provided on the downwardly extending skirt of lid 24. By opening the clasps, lid 24 may be pivoted to the open position.

Figure 2:
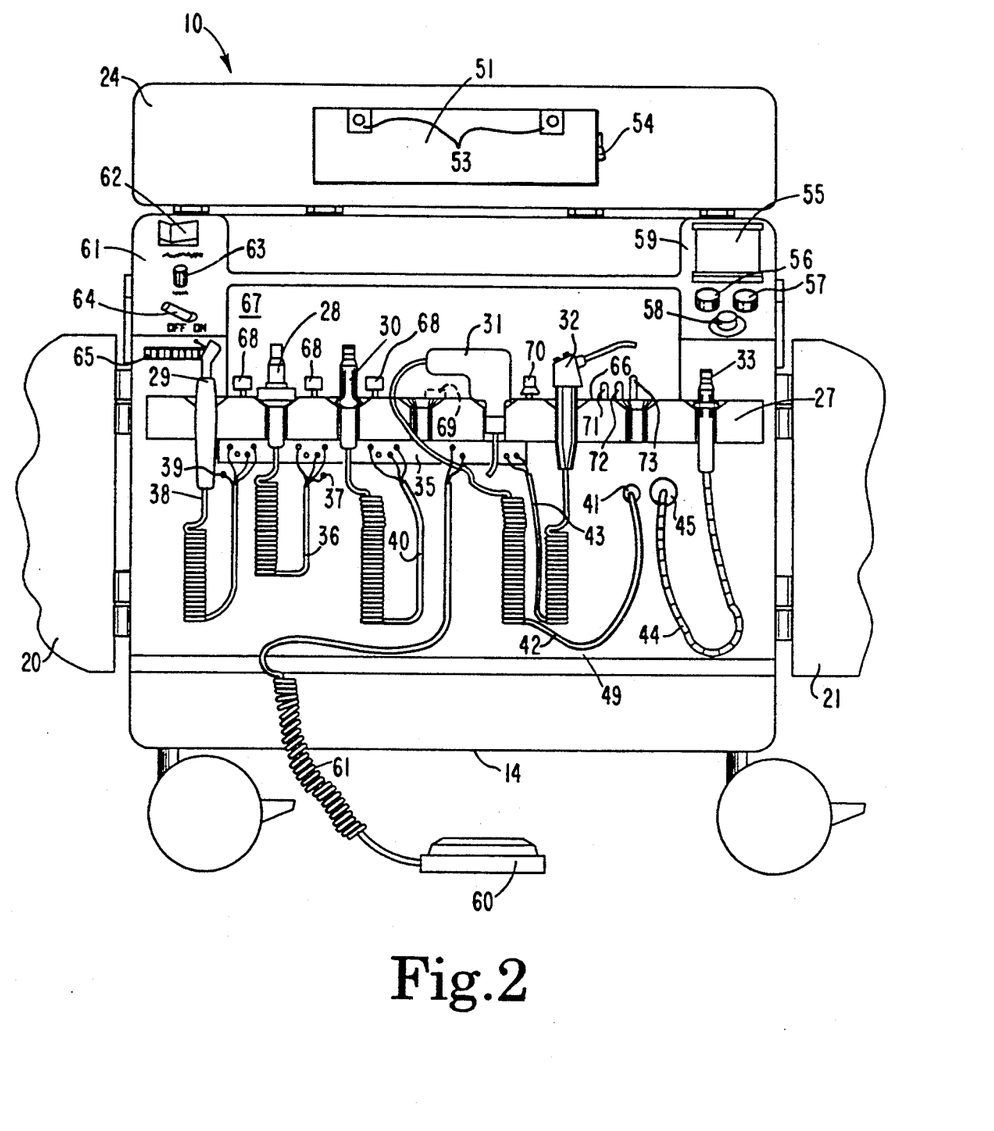
FIG. 2 is a fragmentary front view of the apparatus of FIG. 1 showing the lid and front doors open depicting the various controls and tools.

With the front doors and lid open as shown in FIG. 2, there are depicted six tools 28 through 33 removably mounted to a tool holder 27. Dental tools 28 through 33 are stored within storage cavity 34 (FIG. 3) when the portable dental apparatus is in the transport state, but are removable therefrom when the portable dental apparatus is in an in-use stationary state. Likewise, a tool holder 27 (FIG. 2) is stored within cavity 34 when the portable dental apparatus is in the transport state, but is slideably removable therefrom to hold the plurality of dental tools when the workstation is in use.

The dental tools shown in the embodiment depicted in the drawings include a low speed drill hand piece 28 (FIG. 2), a high speed drill hand piece 29, an ultrasonic air scaler 30, a light curing unit 31, a three-way syringe 32 and a suction hand piece 33. Such dental tools are commercially available and may be purchased for example from the following sources:

| Drill hand pieces | Lares Research Company, 1581 Industrial Road, San Carlos, California 94070 |
| --- | --- |
| Ultrasonic air scaler | Star Dental Products, 1816 Colonial Village Lane Lancaster, Pennsylvania 17601 |
| Light curing unit | Demetrol Research Corporation, 5 Ye Olde Road Danbury, Connecticut 06810 |
| Three-way syringe | Marus Dental International, 20554 Builder Street, Bend, Oregon 97701 |

Low speed drill hand piece 28 is pneumatically driven and has an output rotatable at approximately 20,000 revolutions per minute. Low speed drill hand piece 28 is connected to distribution manifold 35 by cable 36. Low speed drill hand piece 28 requires a compresssed air source, an air vent, and means for emitting water and thus cable 36 includes an air supply line, an air return line, and a water conduit all connected to manifold 35. A fiber optic line is also included in the cable to provide light to the low speed drill hand piece 28. The fiber optic line is connected to light supply port 37.

High speed drill hand piece 29 is pneumatically driven and has an output rotatable at approximately 300,000 revolutions per minute. High speed drill hand piece 29 is connected to distribution manifold 35 by cable 38. High speed drill hand piece 29 requires a compresssed air source, an air vent, and means for emitting water and thus cable 38 includes an air supply line, an air return line, and a water conduit all connected to manifold 35. A fiber optic line is also included in the cable to provide light to the high speed drill hand piece 29. The fiber optic line is connected to light supply port 39.

The ultrasonic air scaler 30 has both a vibratory air outlet and water outlet and requires a compresssed air source, an air vent and means for emitting water. Cable 40, therefore, includes an air supply line, an air return line, and a water conduit which are connected to three outlets provided on distribution manifold 35.

The fourth tool holder recess as viewed from left to right is empty. This recess is provided to accomodate future tool additions.

Light curing unit 31 is connected by fiber optics to a source of light energy within the main housing of the portable dental apparatus. Connection of the light curing unit 31 to the light supply port 41 is by cable 42.

Three-way syringe 32 is operable to emit either compressed air or water depending upon the operation of the controls located on the syringe. Syringe 31 is connected to distribution manifold 35 by cable 43 which has a compressed air conduit and a water conduit therein.

A suction hand piece 33 is connected via hose 44 to suction port 45. Suction is provided by a vacuum unit within the portable dental workstation.

Figure 7:
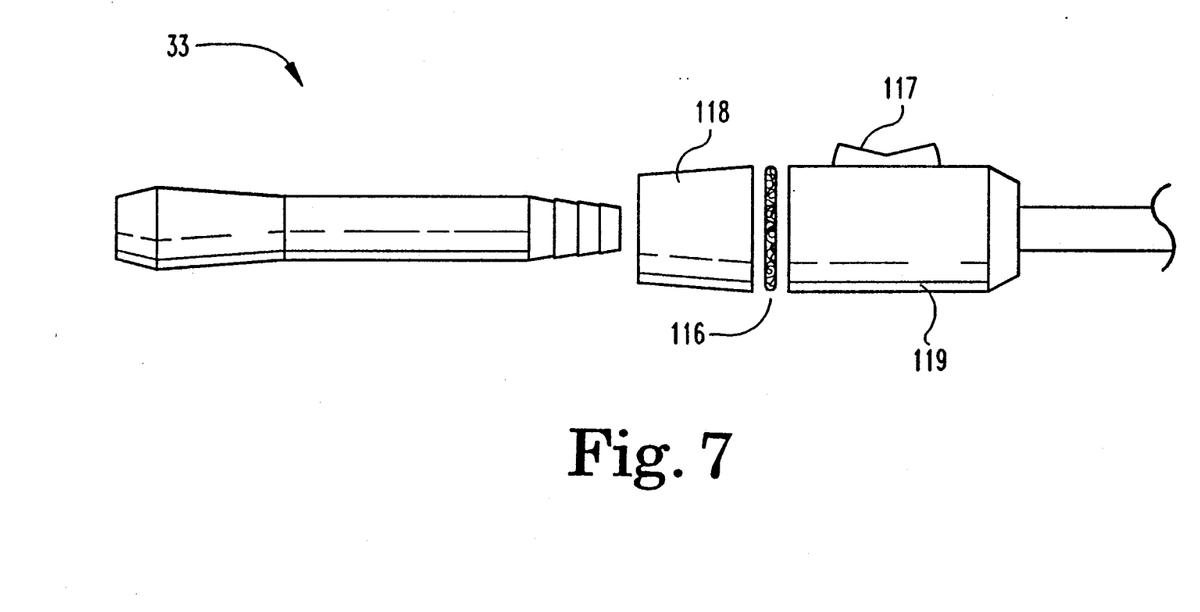
FIG. 7 is a plan view of the suction hand piece of the portable dental apparatus incorporating the present invention.

Suction hand piece 33 includes a three position hermetically sealed electrical rocker switch 116. Rocker switch 116 is connected between vacuum motor 80 and a source of electrical energy and has an on, a momentary on, and an off position. This switch allows the dentist to remotely activate the vacuum motor such that the motor is only running when the dentist requires the use of hand held suction piece 33. This switch therefore reduces wear and tear on the vacuum motor.

Suction hand piece 33 also includes a solid filter 117. Positioning the solid filter 117 in the hand held suction piece 33 enables a dentist to easily clean solids from the suction mechanism. Another advantage of placing solid filter 117 in a hand held piece 33 is to allow a dentist to easily remove tooth remnants for examination, gold fillings and other valuable dental implants once they are sucked into hand held suction piece 33. Hand piece 33 includes two housings 118 and 119 removably secured together by conventional means, such as fasteners or a snap flange with filter 116 located therebetween.

The tools are removably held by holder 27. Tool holder 27 is slidably mounted in a horizontal direction to the front of the housing, is non-removable therefrom, and may hold a total of eight tools. In the embodiment shown in FIG. 2, six tools are shown mounted to the holder with two spare mounting recesses being provided for additional tools.

Tool holder 27 (FIG. 3) has a holder main body 46 fixedly mounted to a pair of rearwardly extending arms 47 and 48 in turn slidably mounted to a recessed front wall 49 of the main housing. The rearwardly extending arms have a T-shaped configuration each of which is received in a T-shaped recess provided in the recessed front wall 49. Arms 47 and 48 may be hollow to allow wires connected between the micro-switches within recesses 50 to extend to the power supply within the housing.

Figure 3:
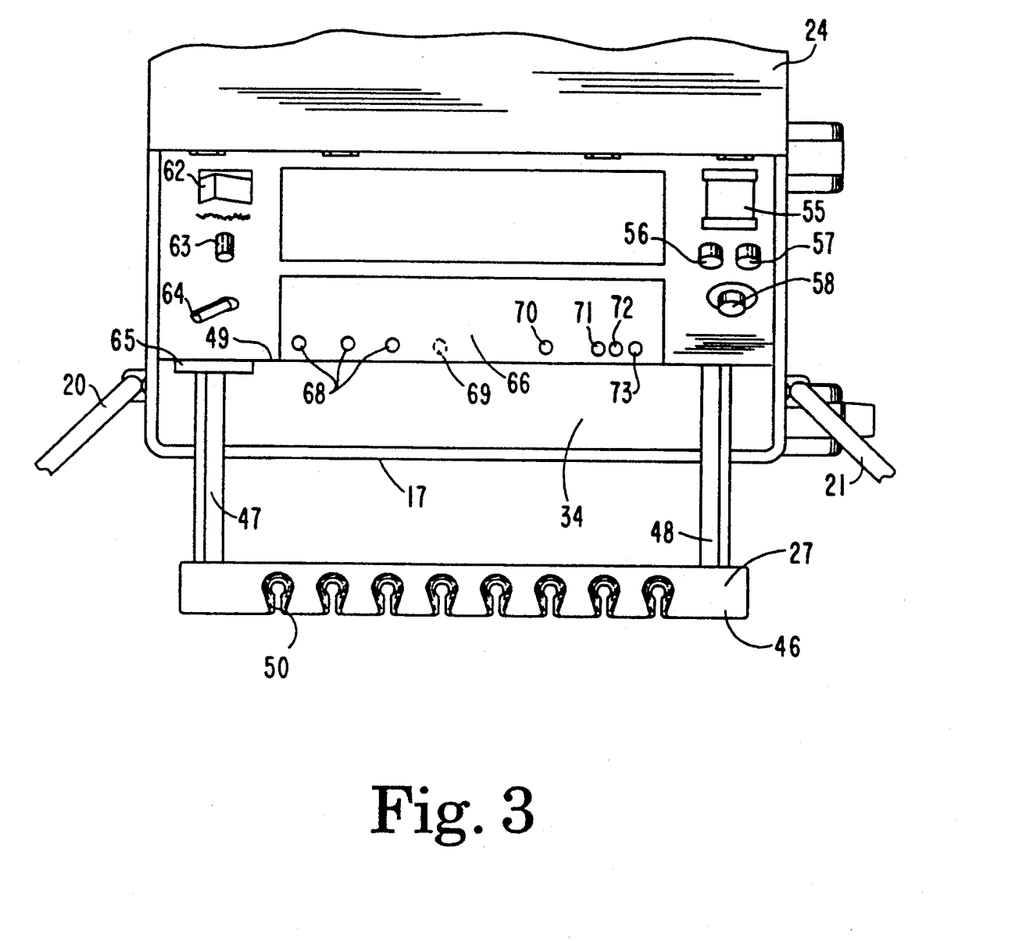
FIG. 3 is a fragmentary top view of the apparatus of FIG. 1.

The tools have been removed from the view in FIG. 3 to illustrate the tool holder recesses 50. Each recess 50 includes a narrow mouth through which the tool may be inserted with the upperwardly facing surfaces being concave or sloped downwardly surrounding each recess 50 to support the enlarged head of each tool. Holders 50, as well as the various tubing and switches shown in the drawings, are available from Marus Dental International, 20554 Builders Street, Bend, Oreg. 97701.

Several of the tools are provided with automatic on-off switches located within the holder recesses 50. Such a switch is found for example within the recesses 50 of tool holder 27 holding tools 28, 29, and 30. The switch takes the form of a spring biased projection which extends into recess 50. When the tool is not mounted to the tool holder the projection extends to the most forward position within the recess thereby turning the tool to the on position. Once the tool is mounted to the tool holder 27 and extends into recess 50 then the tool will contact and depress the micro switch thereby deactivating the tool.

The recessed front wall 49 of main housing 11 is spaced a sufficient distance rearward of the lower front wall 17 of the main housing to allow arms 47 and 48 to be extended completely into the housing thereby positioning holder 27 along with the tools mounted thereto between vertical planes defined by walls 17 and 49. Doors 20 and 21 may then be pivoted closed so as to be vertically aligned with the lower front wall 17 thereby forming a tool storage area 34. Lower front wall 17 extends upwardly from the bottom wall 14 of the main housing forming a storage cavity into which various air lines, electrical cords and a foot pedal may be temporarily stored.

A lightable X-ray display screen 51 is provided on the surface of lid 24 and has a pair of clips 53 for releasably holding an X-ray film. Suitable lighting devices are located behind screen 51 with power being routed thereto by a conventional on/off switch 54 in turn connected to a source of electrical energy within the unit.

A foot pedal 60 is shown below portable dental work station 10. Foot pedal 60 is a pneumatic switch and is connected to distribution manifold 35 by cable 61. Cable 61 contains both an air source line and an air return line.

A conventional amalgamator is mounted below amalgamator door 55. Conventional controls including a three-speed control 56, a timer 57, and a push button start 58 are mounted on control surface 59 and are operably connected between the amalgamator and the source of electrical energy to control the speed and duration of the shaking motion.

A second control surface 61 is shown at the upper left hand corner of portable dental work station 10. Mounted on second control surface 61 is the main power switch 62, water volume control 63, and water on/off switch 64. These controls are connected to distribution manifold 35 and the other components within the cabinet of the portable work station 10.

A pressure gauge 65 is mounted below second control surface 61. Pressure gauge 65 is also connected to distribution manifold 35 in such a way as to provide an air pressure reading when each of the pneumatic tools 28, 29, and 30 are in use.

A third control surface 66 is provided within recess 67 in portable dental work station 10. The first three controls on the left hand side of third control surface 66 are air flow regulators 68. These air flow regulators control the amount of air distributed to low speed drill 28, high speed drill 29, and ultrasonic air scaler 30. A fourth control, shown as a dashed element in FIGS. 2 and 3, is provided to regulate the air to the syringe and the water source. This fourth regulator 69 is adjusted at the factory and is inaccessible to the dentist.

Four additional controls are located on the right hand side of third control surface 66. The left hand most control is a curing light timer 70. Curing light timer 70 is electrically connected to light curing unit 31 to provide a means of controlling the ultraviolet light exposure. The second control moving from left to right is a vacuum motor speed control 71. Vacuum motor speed control 71 allows the dentist to control the amount of vacuum provided to suction hand piece 33.

The remaining two controls on third control surface 66 relate to three way syringe 32. The left hand control 72 controls the water volume to the syringe. The right hand control 73 regulates the air volume to the syringe.

A rear door 74 is hingedly mounted to the back wall 18 of the main housing and includes a pair of clasps which releasably holds the door in the closed position. The clasps are not shown in FIG. 4 due to the cutaway revealing the interior of the unit. The clasps are conventional in nature and function similar to those shown in FIG. 1.

Rear door 74 is shown fragmented and in the open position in FIG. 4 illustrating the interior 75 for holding an air compressor 76, an air holding tank 77, a waste water reservoir tank 78, a fresh water reservoir tank 79, and a vacuum motor 80. Air compressor 76 is electrically connected to a conventional electric power supply in turn having an electric line extending outwardly from the main housing to a source of electrical energy. The electric power supply is mounted behind waste water reservoir tank 78 and as such is not shown in FIG. 4.

Easy access for servicing purposes is provided for the above components due to the modular construction of the portable dental apparatus. This modular construction allows each of the components to be serviced separately if needed and minimizes the amount of time the unit will be out of service. Such construction also allows for maintenance to be performed by technicians with little or no specialized skills.

Compressor 76 is operable to pressurize air holding tank 77 which is provided with suitable valves for safety purposes and for maintaining the air within the tank at a predetermined level. An outlet valve is mounted to the bottom of tank 77 and extends outwardly through the bottom wall of main housing 11 to allow tank 77 to be drained for maintenance purposes.

Air holding tank 77 is connected through foot pedal 60. The air line is then connected to distribution manifold 35 in turn connected to lines 38, 36, and 40 of the high speed drill piece 29, low speed drill piece 28, and ultrasonic air scaler 30. The foot pedal 60 is operable to control the volume of air delivered to the three pneumatic tools 28-30.

Figure 6:
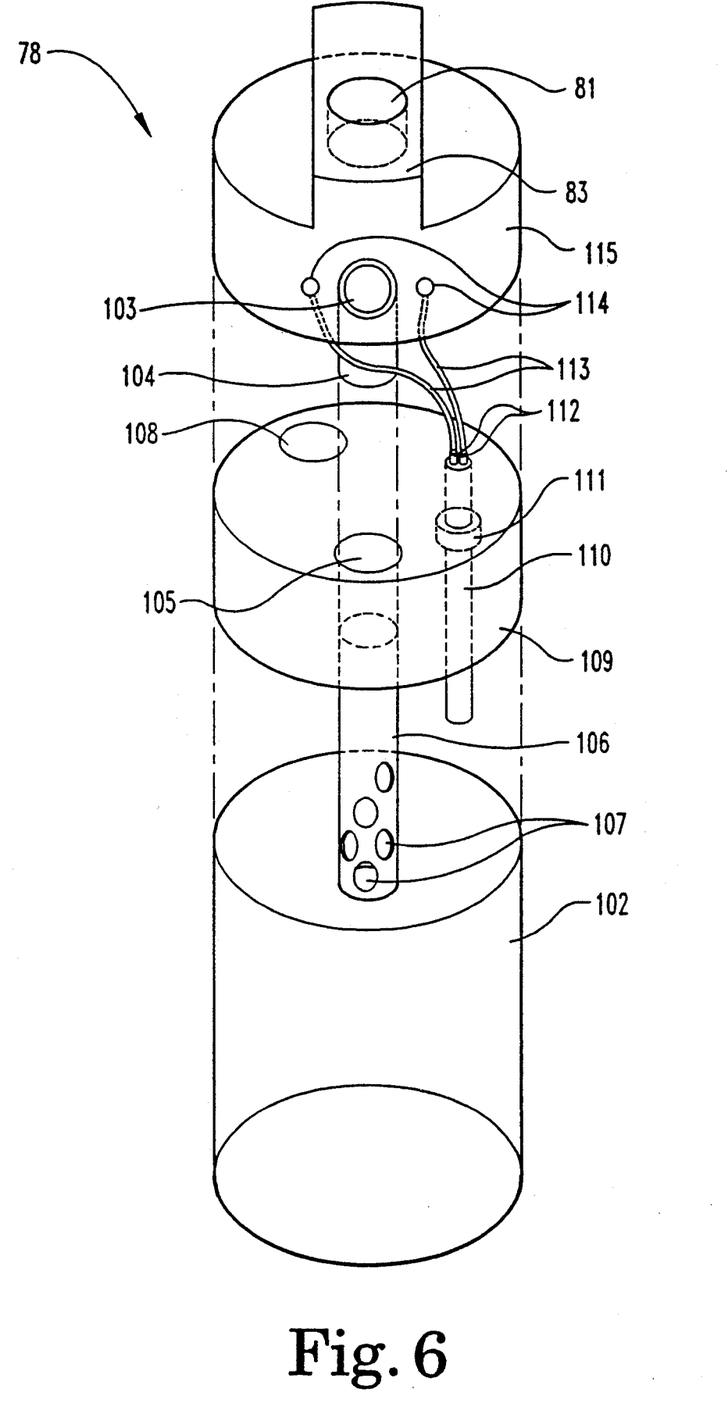
FIG. 6 is an enlarged exploded perspective view of the waste water reservoir of the portable dental apparatus incorporating the present invention.

Vacuum motor 80 is operable to provide suction at the upper portion of waste water reservoir tank 78. This vacuum is applied at vacuum source port 81 as shown in the detailed drawing of waste water reservoir tank 78 (FIG. 6). A slotted member 82 is provided below vacuum source 80 and above waste water reservoir tank 78. This slotted member provides a complementary sized mating surface for container cap guide 83 (FIG. 6). Slotted member 82 is perforated above container guide 83 to allow vacuum air to pass from waste water reservoir tank 78 to vacuum source 80. Slotted member 82 may be of a two-piece construction to allow direct contact between container guide 83 and vacuum source 80.

Fresh water is provided by fresh water reservoir tank 79 which has a first conduit 84 connected to the outlet of air holding tank 77 thereby pressurizing the water within tank 79. The outlet conduit 85 of tank 79 is connected via a check valve 99 (FIG. 5) and water volume control 63 to distribution manifold 35. The distribution manifold 35 in turn is connected a separate water outlet for each line 36, 38, and 40 providing water spray capability to tools 28 through 30.

The three-way syringe 32 is also connected to the fresh water reservoir tank. Additionally, the syringe is connected via air volume control 73 (FIG. 5) to the air holding tank 77.

An on-off switch 62 controls operation of the primary electrical system. Thus, switch 62 controls operation of the compressor and controls current flow to the power supply and all controls.

Compressed air and pressurized water are transmitted to the dental tools through distribution manifold 35. In the preferred embodiment of the invention, distribution manifold 35 is made of plastic or other such suitable material. The manifold contains various ports and passages as well as fastening locations for the valves and controls of the present invention. Distribution manifold 35 is self-contained, minimizing the need for tubing and hoses. Because distribution manifold is made of a solid material it can be threaded to allow the various components to be securely attached to the manifold.

Figure 5:
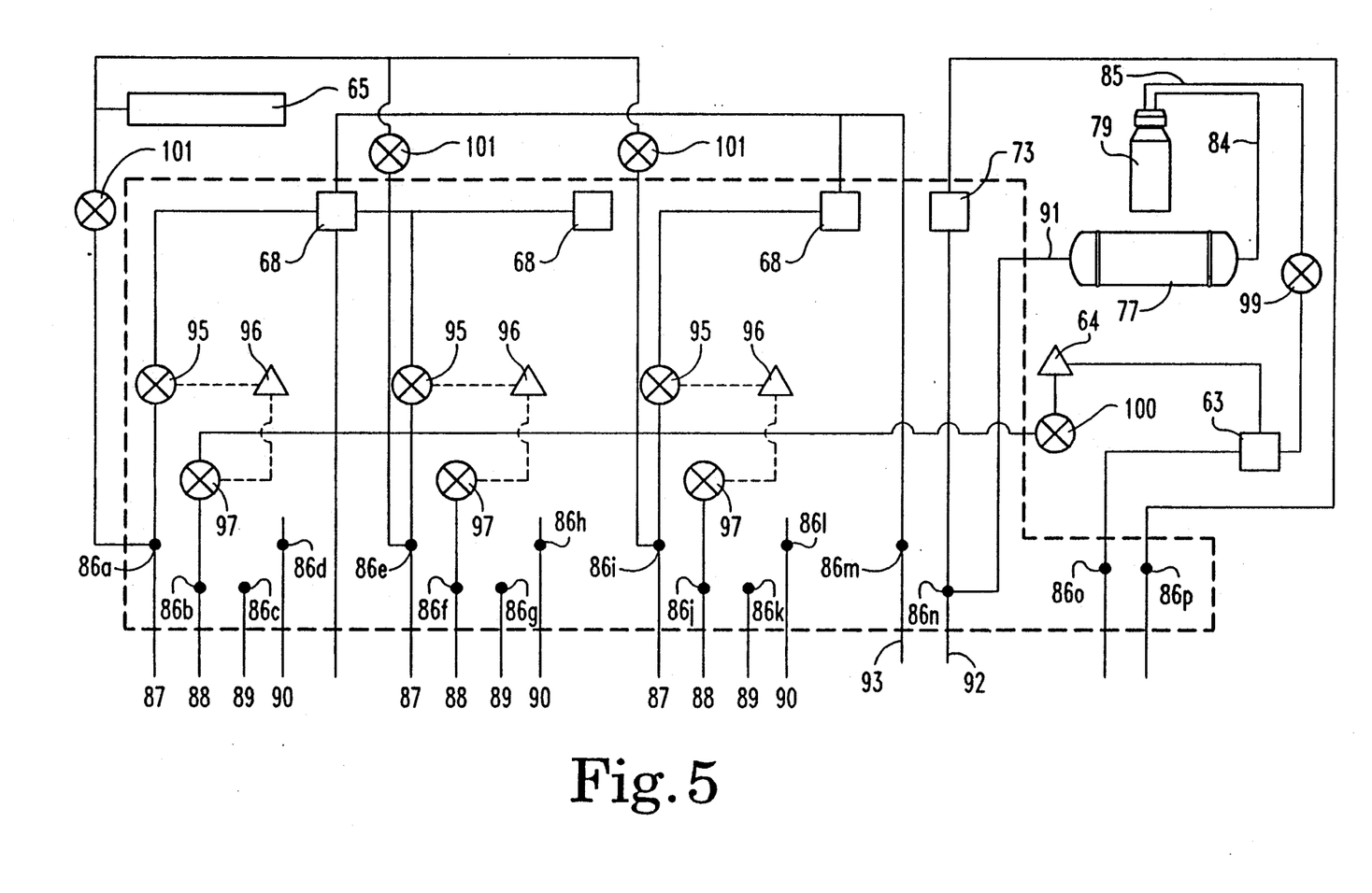
FIG. 5 is a schematic diagram of the distribution manifold and pneumatic system of the portable dental apparatus incorporating the present invention.

A schematic diagram of the internal works of the manifold as well as some of the external connections of the manifold is shown in FIG. 5. The components shown within the dashed box are those components that are directly attached to, or contained within, the distribution manifold 35. All connections between the components within the dashed box are accomplished through the distribution manifold 35.

Connection nodes 86 represent attachment points for dental tool cables 36, 38, 40, 43, and 61 as shown in FIG. 2. Three identical groups of four nodes 86 are provided shown in FIG. 5. These three groups of four nodes 86 are provided for connection to high speed drill 29, low speed drill 28 and ultrasonic scaler 30. A compressed air supply line 87 runs out of the first node of the four node groups. This line supplies compressed air to power the dental tools. A water supply line 88 runs out of the second node to supply pressurized water to the dental tools The third node is provided for a water return line 89 for future use as none of the tools included in the present embodiment require a water return line. The final node in the group of four provides a point of attachment for air return line 90. Any residual air not used by the dental tools is routed from the tool through this line.

Compressed air is conveyed from compressed air tank 77 through a hose 91 to manifold node 86n. Foot pedal air supply line 92 plugs into node 86n and conveys compressed air to foot pedal 60. Foot pedal 60 thus provides a means of manipulating the air supply to the dental tools.

Compressed air leaves the foot pedal and travels to node 86m through foot pedal air return line 93. Foot pedal air return line 93 plugs into node 86m. Compressed air then passes through the distribution manifold 35 to air flow regulators 68. The dentist can control the quantity of air passing to the dental tools by adjusting the air flow regulators 68 with the control knobs shown in FIGS. 2 and 3. Air finally passes from air flow regulator 68 through an on/off air valves 95 to nodes 86a, 86e, and 86i.

Microswitches 96 placed within the tool holders control both air on and off valves 95 and water on/off valves 97. Thus, both compressed air and pressurized water are prohibited from entering the tools unless the tools are moved from the tool holder.

Pressurized water is also conveyed through distribution manifold 35 to the various dental tools. Pressurized water from water supply 79 passes through water line 85 to check valve 99 and then to water volume control 63. The pressurized water next travels toward the dental tools 28-30 by passing through on/off water toggle switch 64 and water relay valve 100. Water relay valve 100 is in turn connected to water on/off valves 97. The output sides of water on/off valves 97 are connected to nodes 86b, 86f and 86j.

A water supply for three way syringe 32 is separately provided for through water volume control 63 and node 86o. The air supply for three way syringe 32 is provided through node 86p which is connected to input regulator 73.

Air supply lines 87 are also connected through check valves 101 to pressure gauge 65. A dentist is, therefore, able to obtain an instantaneous reading of the pressure available as each tool is used.

A detailed drawing of waste water reservoir tank 78 is shown in FIG. 6. Transparent plastic container 102 is used to collect spent water and other fluids from suction hand piece 33.

Suction hand piece 33 is placed in the patient's mouth to vacuum out water and other debris and transmit it through suction hose 44. Suction hose 44 passes through suction port 45 and connects to cap suction tube port 103 of waste water reservoir tank 78. The air, water, and debris pass through 90 degree elbow 104 and lid suction tube port 105 into baffle tube 106. Finally, the air water and debris are transmitted into plastic container 102 through baffle outlet holes 107.

Configuring the vacuum hose and baffle tube in this manner provides a means of settling the liquid as it enters plastic container 102, thus preventing liquid from splashing up toward the vacuum source 80. Vacuum is applied to inside of plastic container 102 through lid vacuum port 108 which is disposed toward the edge of container lid 109 so as to prevent the direct passage of air into vacuum source port 81. This geometry further serves to protect vacuum motor 80.

Waste water reservoir tank 78 also contains a liquid level sensor which serves to shut off the vacuum motor 80 in the event that container 102 becomes full. The liquid level sensor switch includes liquid level sensor switch rod 110, liquid level float 111, electrical contact 112, and sensor wires 113. Sensor wires 113 are connected to container cap electrical contacts 114.

When liquid collects in container 102 it rises causing liquid level sensor switch float 111 to also rise. At a predetermined point the rising float 111 encounters a position on liquid level sensor switch rod 110 where the electrical circuit of sensor becomes open. When this circuit is opened the power to vacuum motor 80 is cut off to prevent the vacuum from drawing any further liquids and debris into container 102.

The upper most portion of waste water reservoir tank 78 is container cap 114. Container cap 114 has a raised portion near the center of the cap that forms container cap guide 83. Container cap guide 83 fits securely into notched member 82 to provide a means of insuring that waste water reservoir tank 78 is properly aligned when placed into the portable work station 10. The use of container cap guide 83 allows for proper alignment of cap suction tube port 103 and container cap electrical contacts 114. Should waste water reservoir tank 78 be improperly installed within the unit, cap electrical contacts 114 will not meet with contacts within the unit. This results in an open circuit to vacuum motor 80 which prevents the vacuum motor from being operated while waste water reservoir tank 78 is an undesirable position.

The portable dental apparatus disclosed herein is totally self contained. Once the apparatus is connected to a source of electrical energy, the tools are immediately operational without requiring any set-up procedures. The preferred embodiment is particularly advantageous in that the tool holder is slidably mounted to the main housing eliminating the need for tool set-up.

While the invention has been illustrated and described in detail in the drawings and foregoing description, the same is to be considered as illustrative and not restrictive in character, it being understood that only the preferred and alternate embodiments have been shown and described and that all changes and modifications that come within the spirit of the invention are desired to be protected.

What is claimed is:

1. A portable dental apparatus comprising:
   a portable main housing having an interior, said main housing including transport means therebeneath operable to allow said portable dental apparatus to have an in-use stationary state and a transport state;
   dental tool holding means on said main housing;
   a plurality of dental tools removably mountable on said dental tool holding means;
   drive means mounted within said interior operable to drive said dental tools, said drive means including a pressurized air source and a pressurized water source;
   a control panel operably associated with said drive means and said plurality of dental tools, said control panel located on said main housing with said main housing sized to form a storage cavity to receive said plurality of dental tools when said portable dental apparatus is in said transport state; and,
   connecting means connected between said drive means and said plurality of dental tools, said connecting means including a distribution manifold and valve means disposed between said drive means and said plurality of dental tools wherein said distribution manifold is substantially solid and includes a plurality of bores, wherein said valve means are connected to said distribution manifold to allow pressurized air and pressurized water to pass from said distribution manifold, through said valve means, and back to into said manifold, and wherein pressurized air and pressurized water are distributed from said pressurized air source and said pressurized water source through said bores and said valves to said plurality of dental tool; and wherein:
   said valve means are mounted to said distributed manifold.

2. The portable dental apparatus of claim 1 wherein:
   said dental tools include a hand held vacuum device; and,
   said drive means includes a vacuum source; and further comprising:
   a waste water reservoir tank connected between said hand held vacuum device and said vacuum source, said waste water reservoir tank having guide means to secure said waste water reservoir tank to said connecting means such that said vacuum source is only operable when said waste water reservoir tank is sealingly engaged to said connecting means.

3. The portable dental apparatus of claim 2 wherein: said waste water reservoir tank has liquid level sensing means to shut off said vacuum source when said waste water reservoir tank is full.

4. The portable dental apparatus of claim 3 wherein: said housing includes a housing frame, an outer housing shell and a rear wall matable with said housing shell, said housing including fastening means removably securing said housing shell and said rear wall to said frame allowing said housing shell and said rear wall to be removed from said housing frame to access modules within said interior.

5. A portable dental apparatus comprising:
a portable main housing having an interior, said main housing including transport means therethrough operable to allow said portable dental apparatus to have an in-use stationary state and a transport state;
dental tool holding means on said main housing;
a plurality of dental tools removably mountable on said dental tool holding means;
drive means mounted within said interior operable to drive said dental tools, said drive means including a pressurized air source and a pressurized water source;
a control panel operably associated with said drive means and said plurality of dental tools, said control panel located on said main housing with said main housing sized to form a storage cavity to receive said plurality of dental tools when said portable dental apparatus is in said transport state; and,
connecting means connected between said drive means and said plurality of dental tools, said connecting means including a distribution manifold and valve means disposed between said drive means and said plurality of dental tools wherein said distribution manifold is substantially solid and includes a plurality of bores, wherein said valve means are connected to said distribution manifold to allow pressurized air and pressurized water to pass from said distribution manifold, through said valve means, and back into said manifold, and wherein pressurized air and pressurized water are distributed from said pressurized air source and said pressurized water source through said bores and said valves to said plurality of dental tools, and wherein;
said housing includes a housing frame an outer housing shell and a rear wall matable with said housing shell, said housing including fastening means removably securing said housing shell and said rear wall to said frame allowing said housing shell and said rear wall to be removed from said housing frame to access modules within said interior;
said dental tools include a hand held vacuum device; and, said drive means includes a vacuum source; and further comprising:
a waste water reservoir tank connected between said hand held vacuum device and said vacuum source, said waste water reservoir tank having a vacuum outlet in communication with said vacuum source and a waste water inlet, said waste water reservoir further having baffle means operable to guide waste water entering said waste water inlet away from said vacuum outlet.

6. The portable dental apparatus of claim 5 wherein: said vacuum source includes a vent opening through said rear wall.

7. A portable dental apparatus comprising:
a portable main housing having an interior, said main housing including transport means therebeneath operable to allow said portable dental apparatus to have an in-use stationary state and a transport state;
dental tool holding means on said main housing;
a plurality of dental tools removably mountable on said dental tool holding means, said dental tools including a hand held vacuum device;
drive means mounted within said interior operable to drive said dental tools, said drive means including a vacuum source;
connecting means connected between said drive means and said plurality of dental tools;
a control panel operably associated with said drive means and said plurality of dental tools; and,
a waste water reservoir tank connected between said hand held vacuum device and said vacuum source, said waste water reservoir tank having guide means to secure said waste water reservoir tank to said connecting means such that said vacuum source is only operable when said waste water reservoir tank is sealingly engaged to said connecting means.

8. The portable dental apparatus of claim 7 wherein: said housing includes a housing frame, an outer housing shell and a rear wall matable with said housing shell, said housing including fastening means removably securing said housing shell and said rear wall to said frame allowing said housing shell and said rear wall to be removed from said housing frame to access modules within said interior.

9. The portable dental apparatus of claim 8 and further comprising:
a container to hold liquid; and,
adjustment means mounted to said housing and disposed between said tools and said container and operable to control flow of liquid to said tools.

10. The portable dental apparatus of claim 9 and further comprising:
rigid manifold means removable mounted to said housing and including a plurality of passages extending therethrough and in fluid communication with said tools and said container operable to allow flow of liquid thereto while providing compact connection therebetween.

11. A portable dental apparatus comprising:
a portable main housing having an interior, said main housing including transport means therebeneath operable to allow said portable dental apparatus to have an in-use stationary state and a transport state;
dental tool holding means on said main housing;
drive means mounted within said interior operable to drive said dental tools, said drive means including a vacuum source;
a plurality of dental tools removably mountable on said dental tool holding means, said dental tools including a hand held vacuum device, said hand held vacuum device including an electric switch to remotely operate said vacuum source;
connecting means connected between said drive means and said plurality of dental tools; and
a control panel operably associated with said drive means and said plurality of dental tools; and
wherein said switch is a three-way switch having an on, momentary on, and an off position.

* * * * *